US00PP34347P2

(12) United States Plant Patent
Garner

(10) Patent No.: US PP34,347 P2
(45) Date of Patent: Jun. 14, 2022

(54) ***PHILODENDRON* PLANT NAMED 'SUMMER GLORY'**

(50) Latin Name: ***Philodendron* hybrid**
Varietal Denomination: Summer Glory

(71) Applicant: Lawrence 'Lariann' Garner, Clewiston, FL (US)

(72) Inventor: Lawrence 'Lariann' Garner, Clewiston, FL (US)

( * ) Notice: Subject to any disclaimer, the term of this patent is extended or adjusted under 35 U.S.C. 154(b) by 48 days.

(21) Appl. No.: 17/300,749

(22) Filed: Oct. 18, 2021

(51) Int. Cl.
*A01H 5/12* (2018.01)
*A01H 6/10* (2018.01)

(52) U.S. Cl.
USPC ..... Plt./381

(58) Field of Classification Search
USPC ..... Plt./373, 381
See application file for complete search history.

*Primary Examiner* — Karen M Redden
(74) *Attorney, Agent, or Firm* — James R. Holm

(57) ABSTRACT

A new and distinct *Philodendron* plant named 'Summer Glory' particularly distinguished by unique reddish bronze colored foliage on young leaves, foliage that turns a dark, shiny green as foliage matures, durability, and relative freedom from pests, is disclosed.

5 Drawing Sheets

Genus and species: *Philodendron* hybrid.
Variety denomination: 'Summer Glory'.

BACKGROUND OF THE NEW PLANT

The present invention comprises a new and distinct interspecific hybrid plant of *Philodendron*, hereinafter referred to by its cultivar name 'Summer Glory'.

The new cultivar was derived from a controlled breeding program conducted by the Inventor at a nursery in Florida City, Fla. The overall purpose of the breeding program is to make new selections of *Philodendron* plants with unique foliage that are cold resistant and durable with a good growth rate in Florida. 'Summer Glory' is the product of a controlled cross made by the inventor in August 2016 between an unnamed hybrid *Philodendron* as the female parent (unpatented) and an unnamed *Philodendron gloriosum* as the male parent (unpatented). 'Summer Glory' was selected by the inventor as a single unique plant in Florida City, Fla. from amongst progeny plants derived from said cross.

The new cultivar was selected based on its distinctive coloration, durability, and relative freedom from pests as compared to other commercially available *Philodendron* cultivars. 'Summer Glory' was first reproduced asexually using in-vitro meristem tip culture in Apopka, Fla. in August 2020. Asexual propagation by in-vitro meristem tip culture of the new cultivar has shown that the unique features of the new cultivar are stable and reproduced true-to-type in successive generations.

Plant Breeder's Rights for this variety have not been applied for. 'Summer Glory' has not been made publicly available or sold anywhere in the world prior to the effective filing date of this application.

SUMMARY OF THE INVENTION

The new *Philodendron* cultivar has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Philodendron* cultivar. The combination of these characteristics distinguishes 'Summer Glory' as a new and distinct variety of *Philodendron:*

1. Unique reddish bronze colored foliage on young leaves;
2. Foliage that turns a dark, shiny green as foliage matures;
3. Durability; and
4. Relative freedom from pests.

DESCRIPTION OF THE PHOTOGRAPHS

This new *Philodendron* cultivar is illustrated by the accompanying colored photographs which show the overall appearance and distinct characteristics of the plant. The colors shown are as true as can be reasonably obtained by conventional photographic procedures. The photographs are of a 3-year-old plant grown in a 2-gallon container under 60 to 90 percent shade in a ploy covered greenhouse in Apopka, Fla. Colors in the photographs may differ slightly from the color values cited in the botanical description which accurately describes the colors of the new variety.

Figure 1:
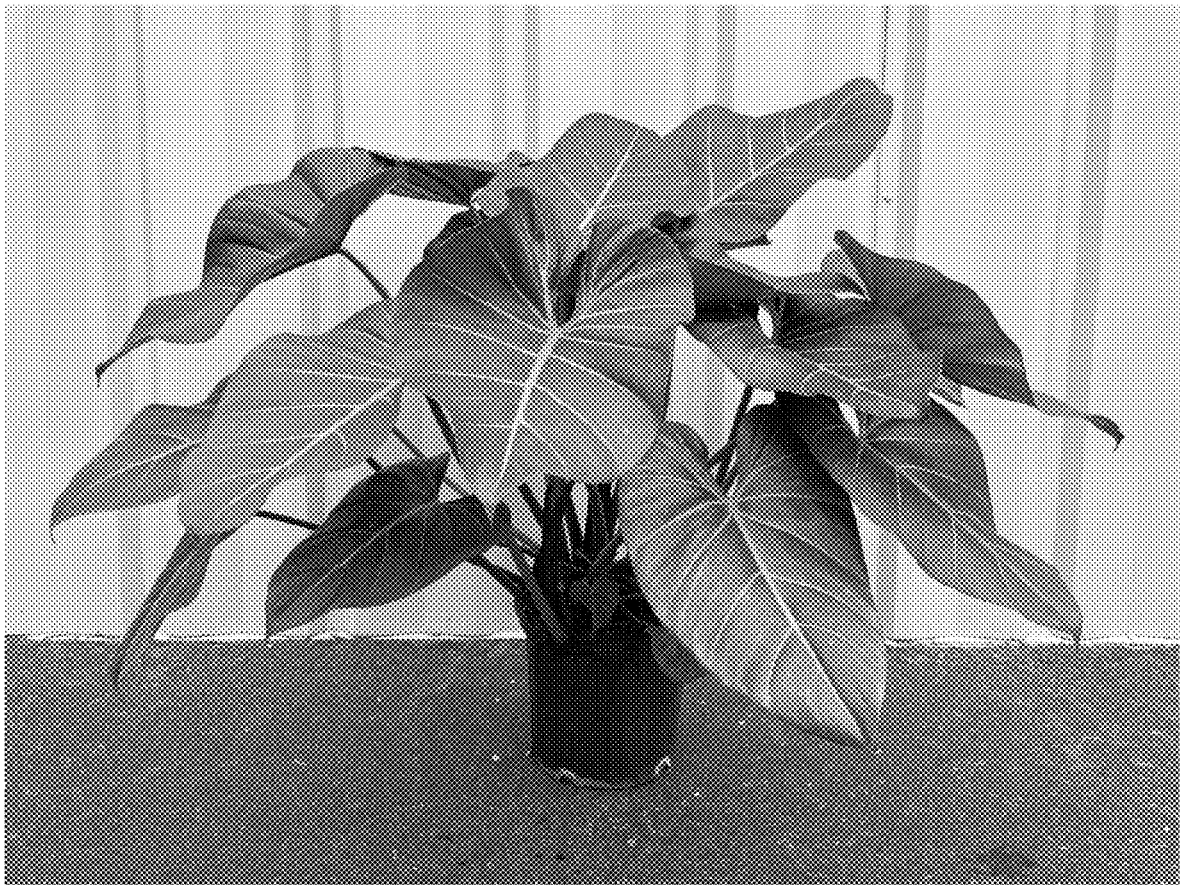

FIG. 1. shows a side view of the overall plant form and foliage of 'Summer Glory'.

Figure 2:
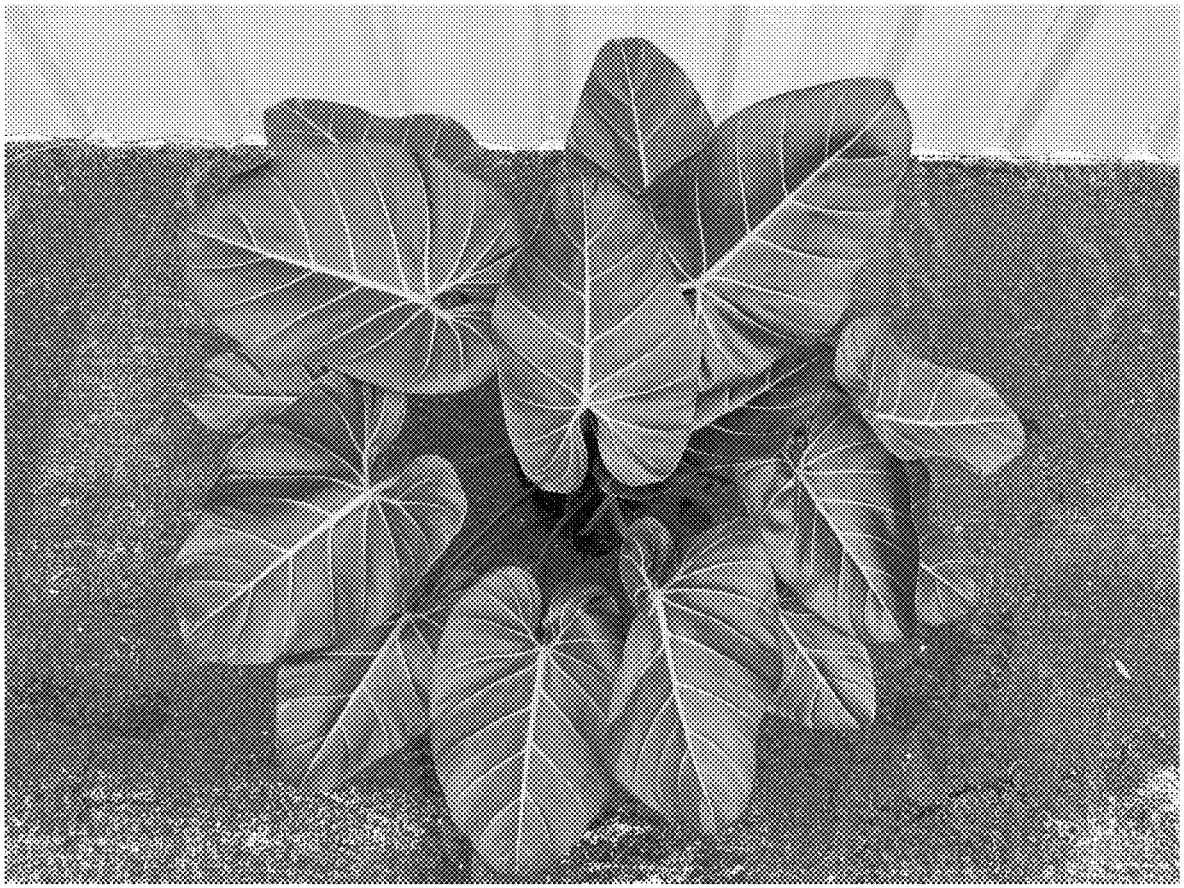

FIG. 2. shows a top view of the overall plant form and foliage of 'Summer Glory'.

Figure 3:
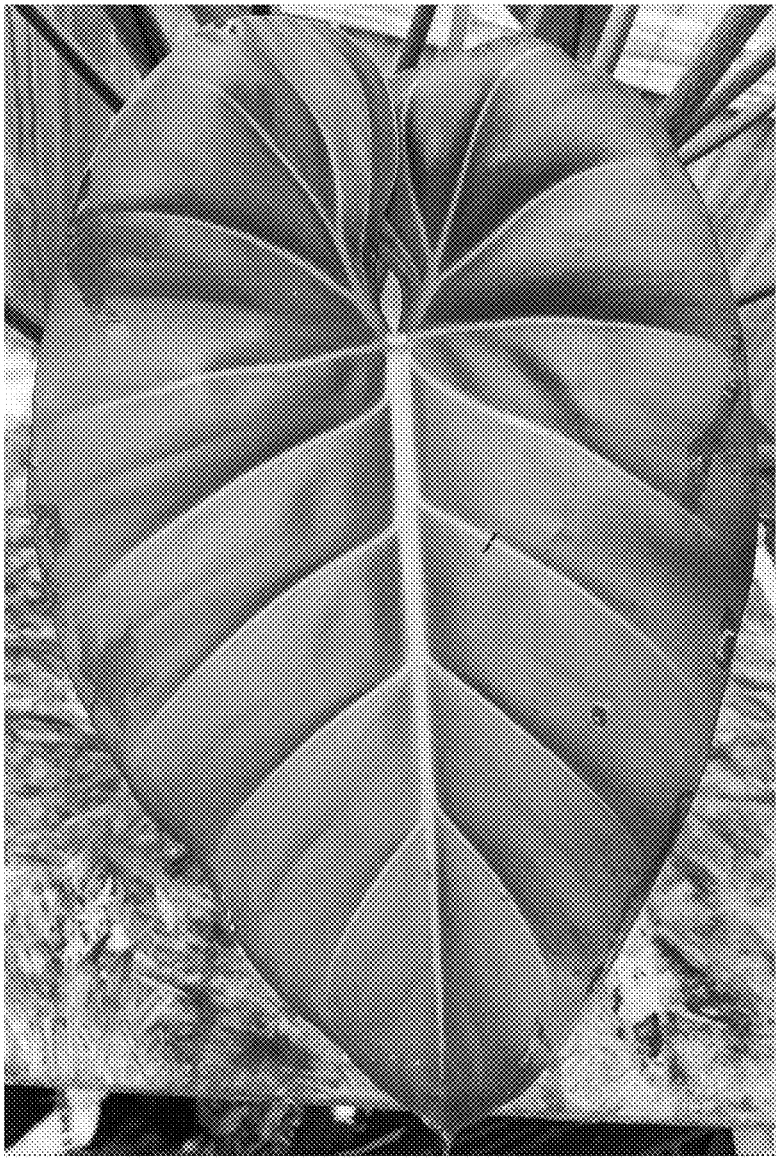

FIG. 3. shows a closeup of a juvenile leaf of 'Summer Glory'.

Figure 4:
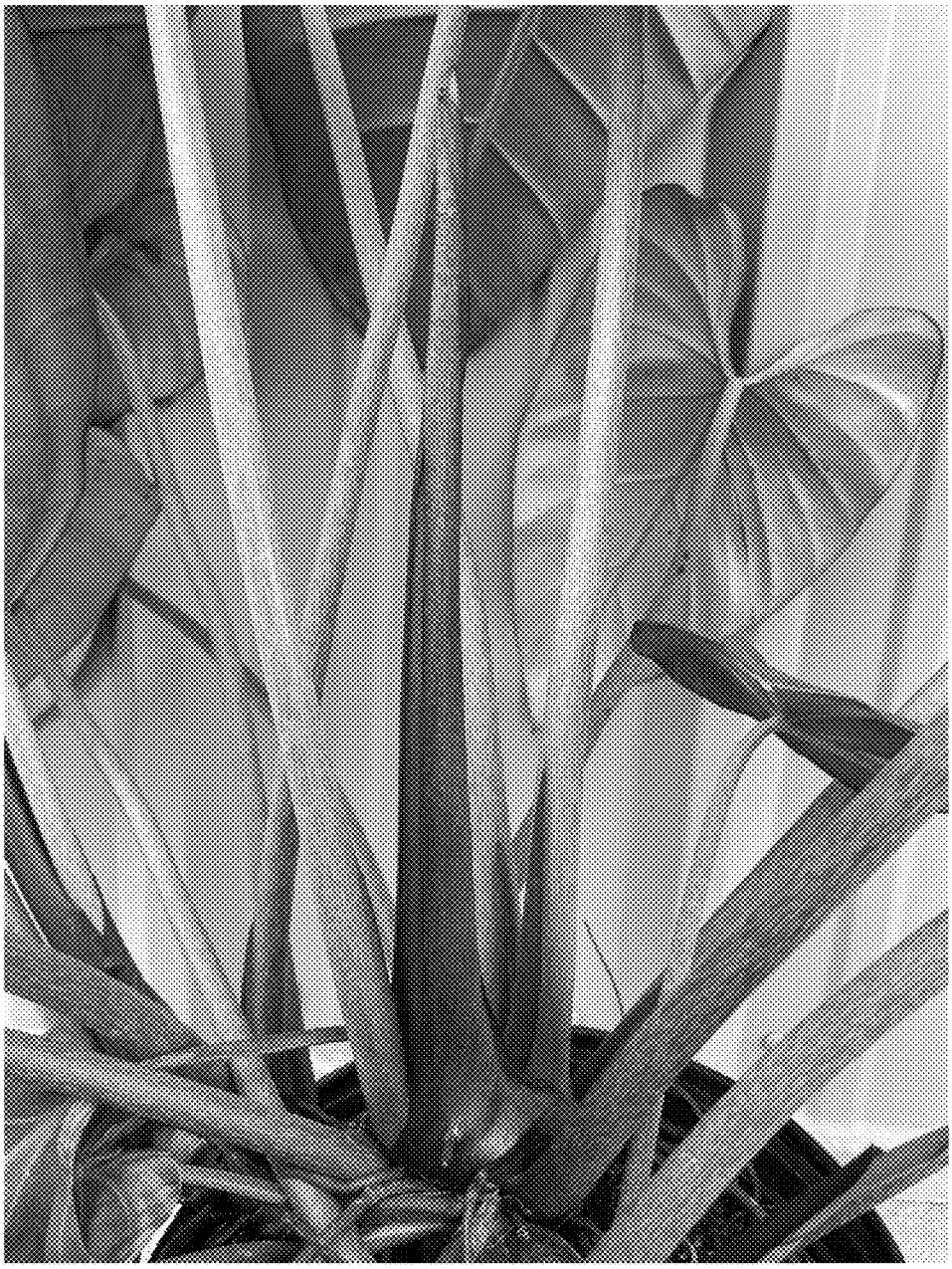

FIG. 4. shows the cataphylls surrounding an emerging leaf of 'Summer Glory'.

Figure 5:
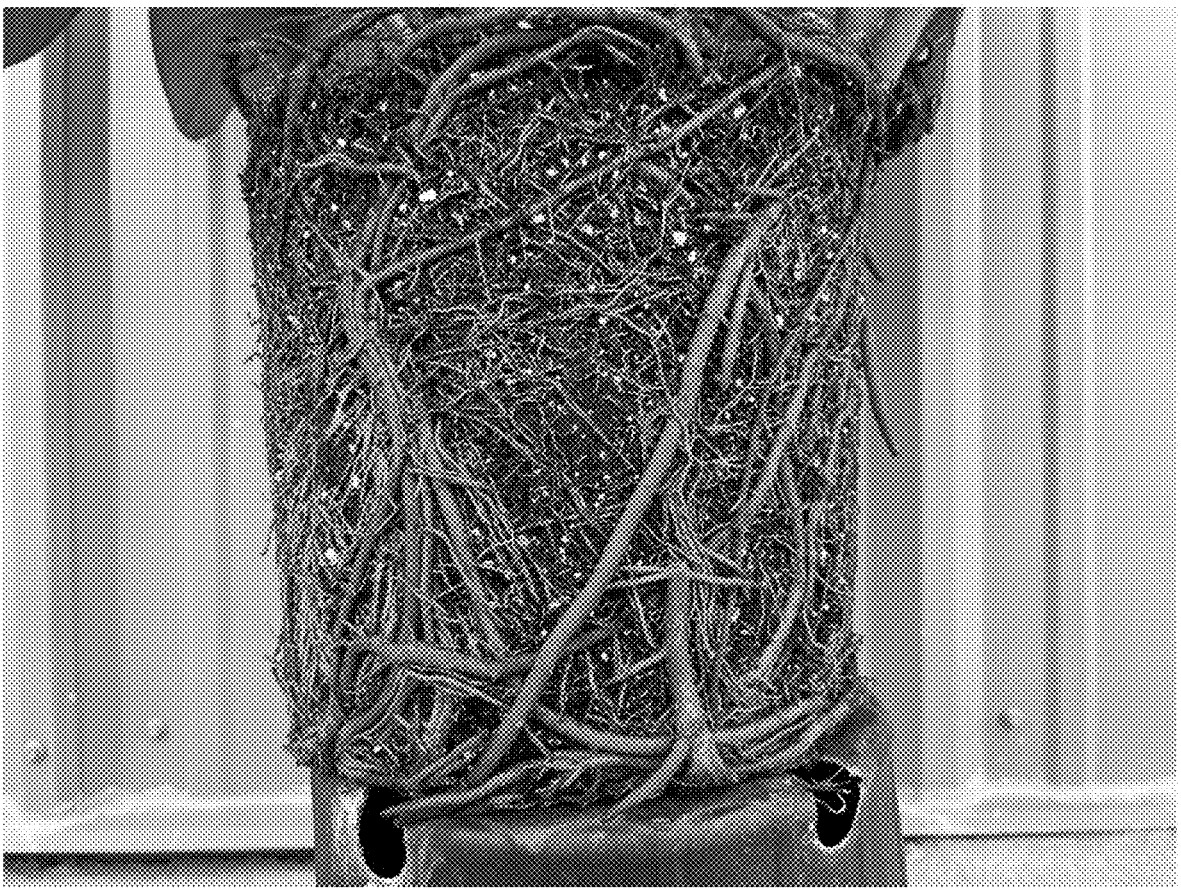

FIG. 5. shows the roots of 'Summer Glory'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown under 60 to 90 percent shade in a poly covered greenhouse in Apopka, Fla. Detailed descriptions were taken in May 2021 from a 3-year-old plant grown in a 2-gallon container. Measurements and numerical values represent averages of typical plant types.

DETAILED BOTANICAL DESCRIPTION

Classification:

*Family*.—Araceae.

*Botanical*.—*Philodendron* hybrid.

*Common*.—*Philodendron*.

*Denomination*.—'Summer Glory'.

General description:

*Plant type*.—Tropical perennial herb.

*Growth habit*.—Upright to arching.

*Height from soil level to top of foliar plane*.—53.34 cm.

*Plant spread*.—91.44 cm.

*Number of basal shoots per plant*.—5.

*Stems*.—Approximately 3.80 cm in diameter.

*Growth rate*.—Moderate.

*Propagation type*.—In-vitro meristem tip culture.

*Time to initiate rooting*.—2 weeks.

*Time to produce a rooted cutting*.—3 weeks.

*Roots*.—Fleshy and fibrous, colored brownish orange, 171B.

Foliage description:

*Quantity of leafs per plant*.—Approximately 16.

*Arrangement*.—Alternate.

*Attachment*.—Petiolate.

*Division*.—Simple.

*Lamina*.—Shape: Cordate-saggitate. Length: 35.6 cm. Width: 22.9 cm. Orientation: Held horizontal to slightly downward. Apex: Aristate. Base: Deeply lobed, lobes about 10.2 cm in depth and 8.9 cm in width, lobes slightly overlap at the base on some leaves. Aspect: Moderately concave. Margins: Entire, slightly to moderately undulate. Texture and luster, adaxial surface: Smooth, glabrous and glossy. Testure and luster, abaxial surface: Smooth, glabrous and moderately glossy. Color: Juvenile foliage, adaxial surface: Reddish bronze, 173A. Juvenile foliage, abaxial surface: Grayish red, 176B, edges are dark red, 183A. Mature foliage, adaxial surface: Overall dark green, NN137A, with faint streaking of yellow-green, NN144A. Mature foliage, abaxial surface: Reddish brown, 177A. Venation: Pattern: Pinnate. Color, adaxial surface: Purplish pink, 186C to 186D on younger foliage, venation color fades with age. Color, abaxial surface: Green, 137B to 137C.

*Petiole*.—Strength: Moderately strong. Shape in cross-section: Very widely ovate. Length: 40.6 cm. Width: 2.54 cm at point of attachment to main stem, narrowing to 0.64 cm at point of attachment to base of lamina. Orientation: Approximately 45 to 60 degrees from the central vertical axis. Texture and luster, adaxial surface: Slightly raised, broken linear striations are present, otherwise glabrous, and slightly glossy. Color: Mostly green, 137B, with a deltoid shaped region at the base colored dark red, 187A to 187B; linear striations are colored gray, 195A, with a slight tint of purplish pink, 186D.

*Cataphyll*.—Description: Double keeled. Shape: Lanceolate. Length: 25.0 cm. Width: 3.8 cm at the base, narrowing towards the apex. Color: Dark red, 59A to 59B, turning lighter red towards the base.

Inflorescence: None observed.

Cold tolerance: Can tolerate down to or near freezing temperatures (30 to 34 degrees F.).

Disease and pest tolerance: Good.

Fruit and seed set: None observed.

Drought tolerance: Good.

COMPARISON WITH PARENTAL VARIETIES

'Summer Glory' differs from the female parent *Philodendron* plant in that 'Summer Glory' has dramatically different and larger leaf shape and color with striking red colored cataphylls surrounding emerging leaves. 'Summer Glory' differs from the male parent *Philodendron* plant in that 'Summer Glory' is much more colorful and more robust.

COMPARISON WITH COMMERCIAL VARIETIES

When 'Summer Glory' is compared to the commercial *Philodendron* plant 'Prince of Orange' (expired U.S. Plant Pat. No. 06,797), the juvenile leaf color on the adaxial surface of 'Summer Glory' is reddish bronze, whereas the juvenile leaf color on the adaxial surface of 'Prince of Orange' is bright orange. Further, 'Summer Glory' has a cordate-saggitate leaf shape with veins colored purplish pink, whereas 'Prince of Orange' has a narrowly ovate leaf shape with veins colored pink. Additionally, the growth habit of 'Summer Glory' is upright to arching with a prominent main stem, whereas the growth habit of 'Prince of Orange' is compact with a very short to near absent main stem.

I claim:

1. A new and distinct variety of *Philodendron* plant named 'Summer Glory', substantially as illustrated and described herein.

* * * * *